United States Patent
Ray, II

(10) Patent No.: US 10,231,924 B2
(45) Date of Patent: *Mar. 19, 2019

(54) COMPOUNDED TOPICAL COMPOSITION AND METHOD

(71) Applicant: CMPD LICENSING, LLC, Conroe, TX (US)

(72) Inventor: Jay Richard Ray, II, Conroe, TX (US)

(73) Assignee: CMPD LICENSING, LLC, Conroe, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/467,386

(22) Filed: Mar. 23, 2017

(65) Prior Publication Data

US 2017/0273897 A1 Sep. 28, 2017

Related U.S. Application Data

(60) Provisional application No. 62/312,290, filed on Mar. 23, 2016.

(51) Int. Cl.
*A61K 31/522* (2006.01)
*A61K 9/00* (2006.01)
*A61K 31/167* (2006.01)
*A61K 9/06* (2006.01)

(52) U.S. Cl.
CPC ............ *A61K 9/0014* (2013.01); *A61K 9/06* (2013.01); *A61K 31/167* (2013.01); *A61K 31/522* (2013.01)

(58) Field of Classification Search
CPC combination set(s) only.
See application file for complete search history.

(56) References Cited

U.S. PATENT DOCUMENTS

| 4,562,060 | A | 12/1985 | Broberg et al. |
| 5,585,379 | A | 12/1996 | Sintov et al. |
| 6,299,902 | B1 | 10/2001 | Won et al. |
| 2013/0165429 | A1* | 6/2013 | Ray, II ............... A61K 31/5415 514/226.5 |
| 2017/0273898 | A1 | 9/2017 | Ray |

FOREIGN PATENT DOCUMENTS

| CN | 104922130 A * | 9/2015 | |
| EP | 1762226 A2 * | 3/2007 | ........... A61K 9/0014 |

OTHER PUBLICATIONS

FDA Label, "Acyclovir Ointment 5%," Valeant Pharmaceuticals International Inc., dated Feb. 2014, accessed Mar. 29, 2016, document of 4 pages, http://www.accessdata.fda.gov/spl/data/b706efb9-e91a-48e5-863f-f1bde3acc382/b706efb9.
drugs.com, "Acyclovir Tablets—FDA prescribing information, side effects and uses," Camber Pharmaceuticals, Inc., dated Jun. 2013, accessed Apr. 12, 2016, document of 11 pages, http://www.drugs.com/pro/acyclovir-tablets.html.
drugs.com, "Lidocaine Cream—FDA prescribing information, side effects and uses," Seton Pharmaceuticals, dated May 2011, accessed Apr. 12, 2016, document of 6 pages, http://www.drugs.com/pro/lidocaine-cream.html.
drugs.com, "Lidocaine Jelly—FDA prescribing information, side effects and uses," Akorn, Inc., dated Oct. 2015, accessed Apr. 12, 2016, document of 10 pages, http://www.drugs.com/pro/lidocaine-jelly.html#s8.
drugs.com, "Lidocaine Ointment—FDA prescribing information, side effects and uses," Gemini Laboratories, LLC, Mar. 2016, accessed Apr. 12, 2016, document of 9 pages, http://www.drugs.com/pro/lidocaine-ointment.html.
PCCA, "PCCA PracaSil™-Plus," PCCA # 30-4655, dated 2013, document of 2 pages.
Pubchem, "SID 24277718," dated Mar. 30, 2007, accessed Apr. 12, 2016, document of 6 pages, http://pubchem.ncbi.nlm.nih.gov/substance/242777718#section=Top.
Taro Pharmaceuticals USA, Inc. (Lidocaine Ointment, https://dailynned.nlnn.nih.gov/dailymed/fda/fdaDrugXsl.cfnn?setid=ae758020-a508-4a2e-8164-e6c324e826a3&type=display, obtained from the Internet Jul. 13, 2018, last revised Apr. 2015) (Year: 2015).

* cited by examiner

*Primary Examiner* — Sudhakar Katakam
(74) *Attorney, Agent, or Firm* — Akerman LLP

(57) ABSTRACT

A compounded topical composition may include an antiviral component, a topical base component, and a local anesthetic component. The antiviral component may include fine powder obtained by grinding oral tablets of one or more antiviral actives. The topical component may include the local anesthetic component. The local anesthetic component may be present in an amount between about 2% and about 8% by weight of the compounded topical composition and the antiviral component may be present in an amount between 4% and 12% by weight of the compounded topical composition. The antiviral component may include acyclovir, valaciclovir, penciclovir, famciclovir, or combinations thereof, and the topical base component may be a lidocaine topical, a lidocaine and prilocaine topical, or both.

19 Claims, No Drawings

COMPOUNDED TOPICAL COMPOSITION AND METHOD

CROSS-REFERENCE TO RELATED APPLICATIONS

The present application claims priority under 35 U.S.C. § 119(e) to U.S. Provisional Patent Application No. 62/312,290, filed on Mar. 23, 2016, which is hereby incorporated by reference into this specification.

TECHNICAL FIELD

The present application relates to compounded pharmacological therapies. In particular, the present application relates to compounded topical compositions for antiviral therapies.

BACKGROUND

Transdermal creams are employed to deliver medication to the skin of a patient. Conventional compositions intended for topical administration include EMLA cream, a eutectic mixture of lidocaine and prilocaine in an emulsified topical cream, such as disclosed by U.S. Pat. Nos. 6,299,902 and 4,562,060, which are incorporated herein by reference in their entireties. However, conventional transdermal creams may include various drawbacks, such as addressing limited medical conditions, creating adverse side effects, and/or having limited shelf lives. Additionally, conventional methods of manufacturing transdermal creams may be inefficient and/or lack precision with the amount of active ingredients, or have other drawbacks.

SUMMARY

A compounded topical composition may include one or more active components. The compounded topical composition may also include a topical base component that includes one or more of the active components. Other active components may be compounded with topical base component to formulate the compounded topical composition.

In various embodiments, active components may include an antiviral component and a local anesthetic component. The compounded topical composition may also include additional active components such as an anti-inflammatory component, an anticonvulsant component, a nerve depressant component, a muscle relaxant component, a NMDA (N-Methyl-D-aspartate) receptor antagonist component, an opiate or opioid agonist component, an antidepressant component, or combinations thereof. The active components may include one or more active agents provided in powder form and that are combined with the topical base component and mixed. In some embodiments, the topical base component may be a commercial cream including all or a portion of one or more active components. For example, the compounded topical composition may include a local anesthetic component comprising local anesthetic active agents selected from lidocaine and prilocaine, wherein all or a portion of the lidocaine, prilocaine, or both are provided in the topical base. In various embodiments, the antiviral component comprises one or more antiviral active agents selected from acyclovir, an acyclovir pro-drug such as valaciclovir, penciclovir, a penciclovir pro-drug such as famciclovir, or combinations thereof. One or more active components may include one or more of the active agents in the form of ground oral tablets that are dissolved, suspended, or combination thereof within the compounded topical composition. For example, all or a portion of the ground tablets may be dissolved while all or a remaining portion of the tablets may be suspended within the compounded topical composition. The dissolved or suspended ground oral tablets may also be dispersed within the compounded topical composition.

In some embodiments, the topical base component includes the local anesthetic component. For example, the topical base component may include a commercial cream, such as component comprising a commercial cream, such as lidocaine 2.5% and prilocaine 2.5% cream or lidocaine 5% ointment to which the antiviral component and, in some embodiments, one or more additional active components are compounded.

In various embodiments, active components may include one or more fine powders including the corresponding active agents. In one example, active agents may be provided in fine powder form generated by grinding up one or more oral tablets containing the active agent. Fine powder may allow for precise amounts of the active agent to be added to the topical base component. In one embodiment, active agents may also be provided in bulk powders, solutions, suspensions, or other formats. The compounded topical composition including fine powder generated from oral tablets may exhibit excellent storage characteristics and avoid separation and/or degradation of the active agent from the base for substantial lengths of time. In some embodiments, one or more active agents may be added to the topical base component in the form of a solution, suspension, emulsion, or bulk powder.

In one aspect, the compounded topical composition may include lidocaine in an amount between about 1% and about 4% by weight of the compounded topical composition; prilocaine in an amount between about 1% and about 4% by weight of the compounded topical composition; and an antiviral component between about 6% and about 10% by weight of the compounded topical composition. In one embodiment, the topical composition may comprise about 2.25% by weight of each of lidocaine and prilocaine and about 8% by weight acyclovir.

In another aspect, a compounded topical composition may include lidocaine in an amount between about 3% and about 6% by weight of the compounded topical composition and an antiviral component between about 6% and about 10% by weight of the compounded topical composition. In one embodiment, the topical composition may comprise about 4.5% by weight lidocaine and about 8% by weight acyclovir.

In another aspect, a method of compounding one or more medications with a topical base component for the topical administration of a compounded topical composition therapy is be provided. The method may include combining an antiviral component with a topical base component. The antiviral component may include one or more antiviral actives selected from acyclovir, an acyclovir pro-drug such as valaciclovir, penciclovir, a penciclovir pro-drug such as famciclovir, or combinations thereof, wherein at least one of the antiviral actives comprises a fine powder of an oral tablet including the antiviral active that is generated by grinding one or more of such oral tablets. Additional antiviral actives, including additional of the antiviral active contained in the fine powder generated from the grinding of oral tablets, may be provided in solution, suspension, emulsion, or bulk powder. In one embodiment, the method includes forming the fine powder of the one or more selected antiviral actives by grinding one or more tablets including the antiviral active. The method may include combining the antiviral component and the topical base component. The antiviral component may be combined with the topical base component in one or more portions. For example, combining may include combining the fine powder including one or more first antiviral actives before or after combining a fine powder or other format include one or more second antiviral actives or additional first antiviral actives with the topical base component.

In one embodiment, the method may include combining a local anesthetic component and the topical base component. The local anesthetic component may be in the form of a solution, suspension, emulsion, bulk powder, or ground oral tablet containing on or more local anesthetic actives of the local anesthetic component. In a further example, the topical base component includes the local anesthetic component or portion thereof. In one formulation, the topical base component comprises a commercial topical composition including at least a portion of the local anesthetic component, such as a lidocaine and prilocaine cream. The method may also include adding the antiviral component and any additional components to the topical base component containing lidocaine or both lidocaine and prilocaine, such that the compounded topical composition includes lidocaine or both lidocaine and prilocaine in an amount of between about 3% to about 6% by weight lidocaine or about 1% to about 4% of each of lidocaine and prilocaine by weight. In further embodiments, the method includes adding an additional component selected from an anti-inflammatory component, an anticonvulsant component, a nerve depressant component, a muscle relaxant component, a NMDA (N-Methyl-D-aspartate) receptor antagonist component, an opiate or opioid agonist component, an antidepressant component, and combinations thereof. The method may include adding ground fine powder of one or more active agents to the topical base component in a sufficient amount such that the compounded topical composition includes the active in an amount of between about 10% and about 25% by weight of the compounded topical composition.

In one aspect, a method of producing a compounded topical composition comprises preparing a fine powder of an antiviral component comprising grinding one or more oral tablets of one or more antiviral actives to obtain a fine powder of the antiviral active; and combining the antiviral component and a topical base component comprising a local anesthetic component and mixing the combined components. The antiviral component may be combined with the topical base component comprising the local anesthetic component in an amount such that the local anesthetic component is present in an amount between about 2% and about 8% by weight of the compounded topical composition and the antiviral component in an amount between 4% and 12% by weight of the compounded topical composition. The antiviral component may comprise one or more antiviral actives selected from acyclovir, valaciclovir, penciclovir, famciclovir, or combinations thereof, and the topical base component may comprise a commercially manufactured/available lidocaine topical, a commercially manufactured/available lidocaine and prilocaine topical, or both. In some embodiments, the antiviral component may be acyclovir, acyclovir and at least one of valaciclovir or famciclovir, valaciclovir, or famciclovir, wherein the topical base component comprises lidocaine 5% ointment, lidocaine 2.5% and prilocaine 2.5% cream, or combination thereof.

In one example, the antiviral component comprises acyclovir and combining the antiviral component and the topical base component comprising the local anesthetic component comprises combining a sufficient amount of fine powder of acyclovir prepared from the grinding of oral tablets of acyclovir to obtain between about 6% and about 9% acyclovir by weight of the compounded topical composition. The topical base component may comprise lidocaine 5% ointment, lidocaine 2.5% and prilocaine 2.5% cream, or combination thereof.

In another example, the antiviral component comprises acyclovir and combining the antiviral component and the topical base component comprising the local anesthetic component comprises combining a sufficient amount of fine powder of acyclovir prepared from the grinding of oral tablets of acyclovir to obtain about 8% acyclovir by weight of the compounded topical composition. The topical base component may comprise lidocaine 5% ointment, lidocaine 2.5% and prilocaine 2.5% cream, or combination thereof.

In yet another example, the antiviral component comprises acyclovir and the topical base component comprises lidocaine 5% ointment, wherein combining the antiviral component and the lidocaine 5% ointment comprises combining a sufficient amount of fine powder of acyclovir prepared from the grinding of oral tablets of acyclovir to obtain between about 6% and about 9% acyclovir and greater than about 4% lidocaine by weight of the compounded topical composition.

In still yet another example, the antiviral component comprises acyclovir and the topical base component comprises lidocaine 5% ointment, wherein combining the antiviral component and the lidocaine 5% ointment comprises combining a sufficient amount of fine powder of acyclovir prepared from the grinding of oral tablets of acyclovir to obtain about 8% acyclovir and about 4.5% lidocaine by weight of the compounded topical composition.

In one example, the antiviral component comprises acyclovir and at least one of valaciclovir or famciclovir and the topical base component comprises lidocaine 5% ointment, wherein combining the antiviral component and the lidocaine 5% ointment comprises combining a sufficient amount of fine powder of acyclovir and at least one of valaciclovir or famciclovir prepared from the grinding of oral tablets of the acyclovir and the at least one of valaciclovir or famciclovir to obtain between about 6% and about 9% acyclovir and the at least one of valaciclovir or famciclovir and greater than about 4% lidocaine by weight of the compounded topical composition.

In another example, the antiviral component comprises acyclovir and at least one of valaciclovir or famciclovir and the topical base component comprises lidocaine 5% ointment, wherein combining the antiviral component and the lidocaine 5% ointment comprises combining a sufficient amount of fine powder of acyclovir and the at least one of valaciclovir or famciclovir prepared from the grinding of oral tablets of acyclovir and the at least one of valaciclovir or famciclovir to obtain about 8% acyclovir and the at least one of valaciclovir or famciclovir and about 4.5% lidocaine by weight of the compounded topical composition.

In yet another example, the antiviral component comprises at least one of valaciclovir or famciclovir and the topical base component comprises lidocaine 5% ointment, wherein combining the antiviral component and the lidocaine 5% ointment comprises combining a sufficient amount of fine powder of the at least one of valaciclovir or famciclovir prepared from the grinding of oral tablets of the at least one of valaciclovir or famciclovir to obtain between about 6% and about 9% of the valaciclovir or famciclovir and greater than 4% lidocaine by weight of the compounded topical composition.

In still yet another example, the antiviral component comprises at least one of valaciclovir or famciclovir and the topical base component comprises lidocaine 5% ointment, wherein combining the antiviral component and the lidocaine 5% ointment comprises combining a sufficient amount of fine powder of the at least one of valaciclovir or famciclovir prepared from the grinding of oral tablets of the at least one of valaciclovir or famciclovir to obtain about 8% of the at least one of valaciclovir or famciclovir and about 4.5% lidocaine by weight of the compounded topical composition.

In one example, the antiviral component comprises acyclovir and the topical base component comprises lidocaine 2.5% and prilocaine 2.5% cream, wherein combining the antiviral component and the lidocaine 2.5% and prilocaine 2.5% cream comprises combining a sufficient amount of fine powder of acyclovir prepared from the grinding of oral tablets of acyclovir to obtain between about 6% and about 9% acyclovir and between about 1.5% and about 2.25% of both lidocaine and prilocaine by weight of the compounded topical composition.

In another example, the antiviral component comprises acyclovir and the topical base component comprises lidocaine 2.5% and prilocaine 2.5% cream, wherein combining the antiviral component and the lidocaine 2.5% and prilocaine 2.5% cream comprises combining a sufficient amount of fine powder of acyclovir prepared from the grinding of oral tablets of acyclovir to obtain about 8% acyclovir and about 2.25% of both lidocaine and prilocaine by weight of the compounded topical composition.

In yet another example, the antiviral component comprises acyclovir and at least one of valaciclovir or famciclovir and the topical base component comprises lidocaine 2.5% and prilocaine 2.5% cream, wherein combining the antiviral component and the lidocaine 2.5% and prilocaine 2.5% cream comprises combining a sufficient amount of fine powder of acyclovir and the at least one of valaciclovir or famciclovir prepared from the grinding of oral tablets of acyclovir and the at least one of valaciclovir or famciclovir to obtain between about 6% and about 9% acyclovir and the at least one of valaciclovir or famciclovir and between about 1.5% and about 2.25% of both lidocaine and prilocaine by weight of the compounded topical composition.

In still yet another example, the antiviral component comprises acyclovir and at least one of valaciclovir or famciclovir and the topical base component comprises lidocaine 2.5% and prilocaine 2.5% cream, wherein combining the antiviral component and the lidocaine 2.5% and prilocaine 2.5% cream comprises combining a sufficient amount of fine powder of acyclovir and the at least one of valaciclovir or famciclovir prepared from the grinding of oral tablets of acyclovir and the at least one of valaciclovir or famciclovir to obtain about 8% acyclovir and the at least one of valaciclovir or famciclovir and about 2.25% of both lidocaine and prilocaine by weight of the compounded topical composition.

In one example, the antiviral component comprises at least one of valaciclovir or famciclovir and the topical base component comprises lidocaine 2.5% and prilocaine 2.5% cream, wherein combining the antiviral component and the lidocaine 2.5% and prilocaine 2.5% cream comprises combining a sufficient amount of fine powder of the at least one of valaciclovir or famciclovir prepared from the grinding of oral tablets of the at least one of valaciclovir or famciclovir to obtain between about 6% and about 9% of the at least one of valaciclovir or famciclovir and between about 1.5% and about 2.25% of both lidocaine and prilocaine by weight of the compounded topical composition.

In another example, the antiviral component comprises at least one of valaciclovir or famciclovir and the topical base component comprises lidocaine 2.5% and prilocaine 2.5% cream, wherein combining the antiviral component and the lidocaine 2.5% and prilocaine 2.5% cream comprises combining a sufficient amount of fine powder of the at least one of valaciclovir or famciclovir prepared from the grinding of oral tablets of the at least one of valaciclovir or famciclovir to obtain about 8% of the at least one of valaciclovir or famciclovir and about 2.25% of both lidocaine and prilocaine by weight of the compounded topical composition.

The above-described and other features and advantages of the present disclosure will be appreciated and understood by those skilled in the art from the following detailed description and appended claims.

DETAILED DESCRIPTION

The present embodiments may relate to a topically deliverable compounded topical composition for treatment of one or more viral ailments related to herpes simplex and varicella zoster, including herpes simplex virus type I (HSV-1) and herpes simplex virus type II (HSV-2). Various embodiments of the compounded topical composition may be formulated and used to prevent or reduce the risk acquisition, spread, or flare-ups/outbreaks of herpes simplex infections, including, but not limited to, labialis, genital, and neonatal infections. The compounded topical composition may be further formulated and used to prevent or reduce the risk of acquisition, spread, or flare-ups/outbreaks of varicella zoster infections, such as chickenpox and shingles. In some embodiments, the topically deliverable compounded topical composition may be formulated and used for treatment of one or more viral ailments related to Epstein-Barr virus and cytomegalovirus.

I. Compounded Topical Compositions

The composition may include a compounded topical composition that includes a topical base component to which one or more active components have been added and mixed. The topical base component may also include one or more active components. One or more active components may include one or more of the active agents in the form of ground oral tablets that disperse within the gel, e.g., the ground oral tablets may be dissolved, suspend, or combination thereof within the compounded topical composition and therein dispersed. Unless indicated otherwise, topical may include formulation for administration to a body surface, such as skin or mucus membrane, and may include local delivery of one or more actives, systemic delivery of one or more actives, or both. Topical may also include formulations for transdermal or transmucosal delivery.

The active components of the compounded topical composition may include an antiviral component and a local anesthetic component. Each active component of the compounded tropical cream includes one or more actives wherein the local anesthetic component comprises one or more local anesthetic actives selected from lidocaine or prilocaine and the antiviral component comprises one or more antiviral actives selected from acyclovir, an acyclovir pro-drug such as valaciclovir, penciclovir, a penciclovir pro-drug such as famciclovir, and combinations thereof.

In one embodiment, a compounded topical composition comprises a topical base component, a local anesthetic component and an antiviral component. Formulating the compounded topical composition may comprise combining the antiviral component with the topical base component and mixing. The antiviral component may comprise one or more antiviral actives selected from acyclovir, an acyclovir pro-drug such as valaciclovir, penciclovir, a penciclovir pro-drug such as famciclovir, and combinations thereof. The local anesthetic component may comprise one or more local anesthetic actives selected from lidocaine, prilocaine, or combination thereof. In one embodiment, formulating the compounded topical composition comprises combining the antiviral component and at least a portion of the local anesthetic component and the topical base component.

The topical base component may include a colloid, emulsion, foam, gel or jelly, cream, ointment, lotion, powder, solution, suspension, spray, aerosol, or other suitable topical base format to deliver the active components. In some embodiments, the topical base component may include all or a portion of one or more active components, such as the local anesthetic component, or one or more active agents thereof. For example, the topical base component may include a lidocaine cream, a lidocaine and prilocaine cream, or both. Such creams may be in the form of a gel, ointment, emulsion, cream, suspension, or other suitable topical format. In some embodiments, the topical base component includes a commercial transdermal cream format that includes all or a portion of the local anesthetic component. As used herein commercial components include commercially manufactured and commercially available products. For example, the topical base may include a lidocaine 2.5% and prilocaine 2.5% cream, such as EMLA or a generic. The topical base may include a lidocaine 5% ointment. In one example, a commercially produced lidocaine and prilocaine cream comprises lidocaine, prilocaine, polyoxyethylene fatty acid esters, sodium hydroxide, purified water, and at least one of carboxypolymethylene or carbomer 934. When the topical base component comprises a commercially available topical cream that includes a portion of an active component, such as local anesthetics in lidocaine 2.5% and prilocaine 2.5% cream or lidocaine 5% cream, the topical composition may be supplemented with additional of such active component via addition of bulk powder, ground oral tablets, solution, suspension, or other format including the active component.

The antiviral component and the topical base component may be combined in amounts such that the compounded topical composition comprises the antiviral component in an amount between about 4% and about 12% by weight of the compounded topical composition and the local anesthetic component in about equivalent amounts of each of lidocaine and prilocaine between about 1.5% and about 2.5% by weight of the compounded topical composition. In another embodiment, the antiviral component and the topical base component may be combined in amounts such that the compounded topical composition comprises the antiviral component in an amount between about 4% and about 12% by weight of the compounded topical composition and the local anesthetic component in an amount of lidocaine between about 2.5% and about 5% by weight of the compounded topical composition.

In one formulation, the topical base component comprises a commercial lidocaine 2.5% and prilocaine 2.5% cream, a commercial lidocaine 5% ointment, or a combination of both and the antiviral component comprises a ground powder generated from grinding commercial oral tablets comprising the antiviral. In on embodiment, additional or supplemental local anesthetic actives may be added to the topical base component before or after the antiviral component is combined with the topical base component. When lidocaine or lidocaine and prilocaine are added or supplemented, the additional or supplemental lidocaine or prilocaine may be in the form of a solution, suspension, emulsion, gel, cream, ointment, powder (which may be a bulk powder or fine ground powder obtained from ground oral tablets), for example. For example, prilocaine may also be added to a lidocaine topical base component, such as lidocaine gel, cream, ointment, or lotion.

In some embodiments, the compounded topical composition comprises one or more additional active components selected from an anti-inflammatory component, an anticonvulsant component, a nerve depressant component, a muscle relaxant component, a NMDA (N-Methyl-D-aspartate) receptor antagonist component, an opiate or opioid agonist component, an antidepressant component, and combinations thereof.

The anti-inflammatory component may include one or more anti-inflammatory actives such as NSAIDS (non-steroidal anti-inflammatory drug) selected from (1) oxicams—meloxicam and piroxicam; (2) salicylic acid derivatives—aspirin, diflunisal, salsalate, and trilisate; (3) propionic acids—flurbiprofen, ibuprofen, ketoprofen, naproxen, and oxaprozin; (4) acetic acids—diclofenac, etodolac, indomethacin, ketorolac, nabumetone, sulindac, and tolmetin; (5) fenamates—meclofenamate; and/or (6) COX-2 inhibitors—celecoxib, rofecoxib, and valdecoxib; and (6) combinations thereof. The anticonvulsant or nerve depressant component may comprise one or more nerve depressants and/or anticonvulsants actives selected from gabapentin, topiramate, lamotrigine. The muscle relaxant component may include one or more muscle relaxant actives selected baclofen, carisoprodol, chlorzoxazone, cyclobenzaprine, dantrolene, diazepam, metaxalone, methocarbamol, orphenadrine, quinine sulfate, tizanidine, and/or other muscle relaxants. The NMDA receptor antagonist component may include one or more NMDA receptor antagonist actives such as ketamine. The opiate or opioid agonist component may comprise one or more opiate or opioid agonist actives selected from tramadol; one or more C2 opiate agonists selected from oxycodone, morphine, methadone, hydromorphone, and fentanyl; one or more C3 opiate agonists selected from hydrocodone, codeine, propoxyphene, butalbital, and pentazocine; or any combination thereof.

In some embodiments, one or more active components or one or more actives thereof may be combined with the topical base component in the form of a solution, suspension, emulsion, or bulk powder.

In various embodiments, one or more of the active components or one or more actives thereof may be in the form of powders combined with the topical base component. The fine powders may be combined with the topical base component and mixed to form the compounded topical composition. The fine powders may be generated form ground oral tablets and combining the active components and the topical base component by addition and mixing may result in the fine powders being dissolved, suspended, or combination thereof within the compounded topical composition and therein dispersed throughout the composition.

In one embodiment, the compounded topical composition includes lidocaine in an amount between about 0.5% and about 4.0% by weight of the compounded topical composition; prilocaine in an amount between about 0.5% and about 4.0% by weight of the compounded topical composition; and an antiviral component between about 4.0% and about 15% by weight of the compounded topical composition, wherein the antiviral component is or comprises acyclovir or one or more actives selected from acyclovir, valaciclovir, penciclovir, famciclovir, and combinations thereof. In another embodiment, the compounded topical composition includes lidocaine in an amount between about 2% and about 6% by weight of the compounded topical composition and an antiviral component between about 4% and about 15% by weight of the compounded topical composition, wherein the antiviral component is or comprises acyclovir or one or more actives selected from acyclovir, valaciclovir, penciclovir, famciclovir, and combinations thereof. In one such example, the compounded topical composition does not include prilocaine.

In one embodiment, the compounded topical composition includes the local anesthetic component comprising lidocaine, prilocaine, or both in an amount between about 2% and about 8% by weight of the compounded topical composition and the antiviral component comprising acyclovir or one or more actives selected from acyclovir, valaciclovir, penciclovir, famciclovir, and combinations thereof in an amount between about 4% and about 12% by weight of the compounded topical composition. In one example, the local anesthetic component includes lidocaine and prilocaine and the antiviral component comprises or is acyclovir or one or more actives selected from acyclovir, valaciclovir, penciclovir, famciclovir, and combinations thereof. In one example of the embodiment, the local anesthetic component includes lidocaine and prilocaine, each in an amount of at least about 1%, about 1.5%, about 2%, about 2.5%, about 3%, about 3.5%, or about 4% by weight of the compounded topical composition and the antiviral component comprises or is acyclovir in an amount of about 4%, about 4.5%, about 5%, about 6%, about 6.5%, about 7%, about 7.5%, about 8%, about 8.5%, about 9%, about 9.5%, about 10%, about 10.5%, about 11%, about 11.5%, or about 12% by weight of the compounded topical composition. In another example, the antiviral component is selected from one or more actives comprising valaciclovir, penciclovir, famciclovir, and combinations thereof, in an amount of about 4%, about 4.5%, about 5%, about 6%, about 6.5%, about 7%, about 7.5%, about 8%, about 8.5%, about 9%. about 9.5%, about 10%, about 10.5%, about 11%, about 11.5%, or about 12% by weight of the compounded topical composition. In another example, the antiviral component includes acyclovir in an amount about 4%, about 4.5%, about 5%, about 6%, about 6.5%, about 7%, about 7.5%, or about 8% by weight of the compounded topical composition and at least one additional active selected from valaciclovir, penciclovir, famciclovir, and combinations thereof, in an amount of about 1%, about 1.5%, about 2%, about 2.5%, about 3%, about 3.5%, or about 4% by weight of the compounded topical composition. In yet another example, the antiviral component comprises or is valaciclovir in an amount of about 4%, about 4.5%, about 5%, about 6%, about 6.5%, about 7%, about 7.5%, about 8%, about 8.5%, about 9%. about 9.5%, about 10%, about 10.5%, about 11%, about 11.5%, or about 12% by weight of the compounded topical composition. In yet still another example, the antiviral component comprises penciclovir, famciclovir, or a combination thereof, in an amount of about 4%, about 4.5%, about 5%, about 6%, about 6.5%, about 7%, about 7.5%, about 8%, about 8.5%, about 9%. about 9.5%, about 10%, about 10.5%, about 11%, about 11.5%, or about 12% by weight of the compounded topical composition. In another example, the local anesthetic component includes lidocaine and prilocaine, each in an amount between about 1.5% and about 2.5%, about 2% and about 2.5%, or about 2.25% by weight of the compounded topical composition and the antiviral component comprises or is acyclovir in an amount between about 5% and about 10%, about 6% and about 9%, about 7% and about 9%, or about 8% by weight of the compounded topical composition. In one example, the antiviral component is selected from one or more actives comprising valaciclovir, penciclovir, famciclovir, and combinations thereof, in an amount between about 5% and about 10%, about 6% and about 9%, about 7% and about 9%, or about 8% by weight of the compounded topical composition. In another example, the antiviral component includes acyclovir in an amount between about 2% and about 8%, about 2% and about 6%, about 2% and about 4%, or about 6% by weight of the compounded topical composition and at least one additional active selected from valaciclovir, penciclovir, famciclovir, and combinations thereof, in an amount between about 1% and about 8%, about 2% and about 6%, about 3% and 5%, about 4% and about 6%, or about 3% by weight of the compounded topical composition. In yet another example, the antiviral component comprises or is valaciclovir in an amount between about 5% and about 10%, about 6% and about 9%, about 7% and about 9%, or about 8% by weight of the compounded topical composition. In yet still another example, the antiviral component comprises penciclovir, famciclovir, or a combination thereof, in an amount between about 5% and about 10%, about 6% and about 9%, about 7% and about 9%, or about 8% by weight of the compounded topical composition.

In one embodiment, the compounded topical composition includes the local anesthetic component in an amount between about 2% and about 8% by weight of the compounded topical composition and the antiviral component in an amount between about 4% and about 12% by weight of the compounded topical composition wherein the local anesthetic component comprises lidocaine and little or no prilocaine. In one example, the antiviral component is acyclovir or one or more actives selected from acyclovir, valaciclovir, penciclovir, famciclovir, and combinations thereof. In a further example, the anesthetic component is lidocaine and the compounded topical composition does not include prilocaine. In one example of the embodiment, the local anesthetic component is or includes lidocaine and the antiviral component is or comprises acyclovir or one or more actives selected from acyclovir, valaciclovir, penciclovir, famciclovir, and combinations thereof. In other such examples, the local anesthetic component comprises or is lidocaine and the antiviral component comprises or is acyclovir or one or more actives selected from acyclovir, valaciclovir, penciclovir, famciclovir, and combinations thereof. In one example, the local anesthetic component comprises or is lidocaine in an amount of at least about 1%, about 1.5%, about 2%, about 2.5%, about 3%, about 3.5%, or about 4% by weight of the compounded topical composition and the antiviral component comprises or is acyclovir in an amount of about 4%, about 4.5%, about 5%, about 6%, about 6.5%, about 7%, about 7.5%, about 8%, about 8.5%, about 9%, about 9.5%, about 10%, about 10.5%, about 11%, about 11.5%, or about 12% by weight of the compounded topical composition. In another example, the antiviral component is selected from one or more actives comprising valaciclovir, penciclovir, famciclovir, and combinations thereof, in an amount of about 4%, about 4.5%, about 5%, about 6%, about 6.5%, about 7%, about 7.5%, about 8%, about 8.5%, about 9%. about 9.5%, about 10%, about 10.5%, about 11%, about 11.5%, or about 12% by weight of the compounded topical composition. In another example, the antiviral component comprises acyclovir in an amount about 4%, about 4.5%, about 5%, about 6%, about 6.5%, about 7%, about 7.5%, or about 8% by weight of the compounded topical composition and at least one additional active selected from valaciclovir, penciclovir, famciclovir, and combinations thereof, in an amount of about 1%, about 1.5%, about 2%, about 2.5%, about 3%, about 3.5%, or about 4% by weight of the compounded topical composition. In yet another example, the antiviral component comprises or is valaciclovir in an amount of about 4%, about 4.5%, about 5%, about 6%, about 6.5%, about 7%, about 7.5%, about 8%, about 8.5%, about 9%. about 9.5%, about 10%, about 10.5%, about 11%, about 11.5%, or about 12% by weight of the compounded topical composition. In yet still another example, the antiviral component comprises penciclovir, famciclovir, or a combination thereof, in an amount of about 4%, about 4.5%, about 5%, about 6%, about 6.5%, about 7%, about 7.5%, about 8%, about 8.5%, about 9%. about 9.5%, about 10%, about 10.5%, about 11%, about 11.5%, or about 12% by weight of the compounded topical composition. In another example, the local anesthetic component is lidocaine in an amount between about 2% and about 8%, about 3% and about 7%, about 4% and about 6%, about 4% and about 5%, or about 4.5% by weight of the compounded topical composition and the antiviral component includes acyclovir in an amount between about 5% and about 10%, about 6% and about 9%, about 7% and about 9%, or about 8% by weight of the compounded topical composition. In one example, the antiviral component is selected from one or more actives comprising valaciclovir, penciclovir, famciclovir, and combinations thereof, in an amount between about 5% and about 10%, about 6% and about 9%, about 7% and about 9%, or about 8% by weight of the compounded topical composition. In another example, the antiviral component includes acyclovir in an amount between about 2% and about 8%, about 2% and about 6%, about 2% and about 4%, or about 6% by weight of the compounded topical composition and at least one additional active selected from valaciclovir, penciclovir, famciclovir, and combinations thereof, in an amount between about 1% and about 8%, about 2% and about 6%, about 3% and 5%, about 4% and about 6%, or about 3% by weight of the compounded topical composition. In yet another example, the antiviral component comprises or is valaciclovir in an amount between about 5% and about 10%, about 6% and about 9%, about 7% and about 9%, or about 8% by weight of the compounded topical composition. In yet still another example, the antiviral component comprises penciclovir, famciclovir, or a combination thereof, in an amount between about 5% and about 10%, about 6% and about 9%, about 7% and about 9%, or about 8% by weight of the compounded topical composition.

In one embodiment, the topical composition comprises about 2.25% by weight lidocaine and prilocaine, respectively, and about 8% by weight acyclovir. In another embodiment, the topical composition comprises about 4.5% by weight lidocaine and about 8% by weight acyclovir. In one such embodiment, the compounded composition does not include prilocaine.

In any of the above embodiments, the compound topical composition may include one or more additional active components. In one example, the compounded topical composition includes an anti-inflammatory component comprising one or more actives, such as flurbiprofen or nabumetone, in an amount between about 5.0% and about 25.0% of the topical composition by weight. In this or another example, the compounded topical composition includes a nerve depressant component comprising one or more actives, such as gabapentin, in an amount between about 5.0% and about 15.0% of the compounded topical composition by weight. In either of the above or another example, the compounded topical composition includes a muscle relaxant component comprising one or more actives, such as cyclobenzaprine, in an amount between about 0.5% and about 4.0% by weight of the compounded topical composition. In one embodiment, the compounded topical composition may comprise about 2.0% lidocaine, about 2.0% prilocaine, about 4.5% lidocaine, about 8% acyclovir and at least one of about 4% to 6% gabapentin, about 0.5% to 1.0% cyclobenzaprine, and about 5% to about 10% flurbiprofen or about 10% to about 20% nabumetone. In one embodiment, acyclovir is present in the compounded topical composition in an amount about 1% to about 10%, about 4% to about 9%, or about 5% to about 8% by weight and lidocaine or lidocaine and prilocaine are present in the compounded topical composition an amount about 4% to about 5% by weight. Additional active components may also be present such as about 1% to about 10% gabapentin, about 1% to about 10%, about 2% to about 8%, about 3% to about 7%, or about 4% to about 6% by weight diclofenac, about 0.5% to about 2%, about 0.5% to about 1.5% by weight cyclobenzaprine.

II. Methods of Compounding

A method of compounding one or more medications with a topical base component for the topical administration of a compounded topical composition is provided.

The method may include combining one or more active components or actives thereof and the topical base component and mixing, which may include milling in an ointment mill. One or more of the active components or actives thereof may be added to the topical base component as a solution, suspension, colloid, emulsion, bulk powder, or ground oral tablet. Thus, the method may include preparing the one or more active components or one or more actives thereof for addition to the topical base component. In one example, preparing the one or more active components or one or more actives thereof for addition to the topical base component includes grinding commercial oral tablets comprising the actives. In this or another example, preparing the one or more active components or one or more actives thereof for addition to the topical base component comprises dissolving, solubilizing, wetting, or suspending one or more actives in solution. The actives may be ground oral tablets or bulk powder. Dissolving, solubilizing, wetting, or suspending may include combining the one or more actives with water for injection or irrigation, DMSO, alcohol, or other suitable liquid.

In one embodiment, the method includes forming a fine powder of an antiviral component comprising grinding up one or more antiviral oral tablets and combining the antiviral component and the topical base component. In this or another embodiment, the method may include combining the local anesthetic component and the topical base component. The local anesthetic component may be in the form of a solution, suspension, emulsion, bulk powder, or find ground oral tablet containing on or more local anesthetics of the local anesthetic component. Thus, the method may include grinding oral tablets of one or more local anesthetic actives. In a further example, the topical base component includes the local anesthetic component or portion thereof. In one formulation, for example, the topical base component comprises a commercial transdermal cream including the local anesthetic component such as a lidocaine or lidocaine and prilocaine cream, which may include a gel, ointment, or emulsion. The fine powder of active agents may be added to the topical base containing lidocaine or both lidocaine and prilocaine, such that the compounded topical composition includes lidocaine or both lidocaine and prilocaine in an amount by weight of the compounded topical composition described above.

A method of compounding may include providing a topical base component having one or more local anesthetics; and adding to the base a fine powder of medication comprising: one or more antiviral actives of the antiviral component. In a further example, the method may further include adding to the topical base component a fine powder of actives of one or more additional components. The one or more additional components may be selected from an anti-inflammatory component, an anticonvulsant component, a nerve depressant component, a muscle relaxant component, a NMDA (N-Methyl-D-aspartate) receptor antagonist component, an opiate or opioid agonist component, an antidepressant component, and combinations thereof. One, more, of all actives of the additional components may be added to the topical base component in the form of a solution, suspension, emulsion, bulk powder, or ground commercial tablet. In one such embodiment, the method may include preparing a one or more of the actives of the additional components for addition to the topical base component comprising grinding commercial tablets comprising the actives to form a fine powder.

As described above, the active agents in fine powder form may be generated from grinding up oral tablets containing the active agent. The compounded topical composition may include the ground tablets dissolved or suspended, including partially dissolved or suspend, within the body of the composition. The fine powder may allow for precise amounts of the active agents to be added to the base. The ground tablets dissolved, suspended, or both may be dispersed throughout the compounded topical composition. The compounded topical composition may exhibit excellent storage characteristics, and avoid separation and/or degradation of the active agents from the base for substantial lengths of time.

The method may comprise providing a topical base component comprising one or more local anesthetic actives of the local anesthetic component. Primary examples of local anesthetics that the topical compositions and base composition disclosed herein may employ include, but are not limited to, lidocaine, prilocaine, benzocaine, and/or tetracaine. In some embodiments, the topical base component includes a commercial transdermal format that includes all or a portion of the local anesthetic component. For example, the topical base component may include lidocaine and prilocaine cream (e.g., EMLA cream or generic), lidocaine cream, or other topical base comprising lidocaine, prilocaine, or both, formulated to topically deliver lidocaine, prilocaine, or both at skin or mucous membrane. In one embodiment, the local anesthetic component may comprise between about 2% and about 6.0% by weight of the compounded topical composition. Other amounts may be used, including those discussed elsewhere herein. The topical base component may include additional, fewer, or alternate ingredients. Preferably, the topical base component may include lidocaine and/or prilocaine. In one embodiment, the topical base component may comprise an equal amount of lidocaine and prilocaine, such as between about 2.0% and about 3.0% by weight. Other amounts may be used, including those discussed elsewhere herein.

The method may comprise combining an additional active component and the topical base component comprising an anti-inflammatory component. The anti-inflammatory component may one or more NSAIDS. The anti-inflammatory component may include one or more of the active agents added to the topical base component in the form of a solution, suspension, emulsion, or fine powder. In one example, the compounded topical composition includes between about 1% and about 5% by weight anti-inflammatory component wherein the anti-inflammatory component comprises at least one NSAID selected from meloxicam, piroxicam, flurbiprofen, ketoprofen, naproxen, oxaprozin, diclofenac, nabumetone. Other anti-inflammatory actives or amounts may be used, including those discussed elsewhere herein.

The method may comprise combining an additional active component and the topical base component comprising an anticonvulsant component. The aanticonvulsant component may include one or more of the active agents added to the topical base component in the form of a solution, suspension, emulsion, or fine powder. In one example, the compounded topical composition includes between about 1% and about 5% by weight anticonvulsant component wherein the anticonvulsant component comprises at least one of lamotrigine or topiramate. Other anticonvulsant actives and amounts may be used, including those discussed elsewhere herein.

The method may comprise combining an additional active component and the topical base component comprising a nerve depressant component. The nerve depressant component may include one or more of the active agents combined with the topical base component in the form of a solution, suspension, emulsion, or fine powder. In one example, the compounded topical composition includes between about 1% and about 5% by weight nerve depressant component wherein the nerve depressant component comprises gabapentin. Other nerve depressant actives and amounts may be used, including those discussed elsewhere herein.

The method may comprise combining an additional active component and the topical base component comprising a muscle relaxant component. The muscle relaxant component may include one or more of the active agents added to the topical base component in the form of a solution, suspension, emulsion, or fine powder. In one example, the compounded topical composition includes between about 1% and about 5% by weight muscle relaxant component wherein the muscle relaxant component comprises cyclobenzaprine. Other muscle relaxant actives and amounts may be used, including those discussed elsewhere herein.

The method may comprise combining an additional active component and the topical base component comprising a NMDA receptor antagonist component. The NMDA receptor antagonist component may include one or more of the active agents added to the topical base component in the form of a solution, suspension, emulsion, or fine powder. In one example, the compounded topical composition includes between about 1% and about 5% by NMDA receptor antagonist component wherein the NMDA receptor antagonist component comprises ketamine. Other NMDA receptor antagonist actives and amounts may be used, including those discussed elsewhere herein.

The method may comprise combining an additional active component and the topical base component comprising an opiate or opioid agonist component. The opiate or opioid agonist component may include one or more of the active agents added to the topical base component in the form of a solution, suspension, emulsion, or fine powder. In one example, the compounded topical composition includes between about 1% and about 5% by weight opiate or opioid agonist component wherein the opiate or opioid agonist component comprises one or more of the C2 and C3 opiate agonists named above, tramadol, or a combination thereof.

Other opiate or opioid agonist actives and amounts may be used, including those discussed elsewhere herein.

In one embodiment, the method may include addition of excipients to the topical base component. In another embodiment, the method does not include addition of excipients to the topical base component. For example, in one embodiment the topical base component includes a commercially manufactured composition containing all or a portion of the local anesthetic component, such as lidocaine and prilocaine cream, gel, ointment, lotion, etc. or lidocaine cream, gel, ointment, lotion, etc., and the method does not include addition of excipients, e.g., additional excipients to the topical base component.

A method of compounding active components with a topical base component using a fine powder of one or more actives is disclosed herein. In this embodiment, a topical base component, such as a commercial lidocaine or lidocaine and prilocaine cream, should be selected. The preparer, such as a pharmacist, should calculate the weight of powders needed. Then, the prepare should grind the actives, such as oral tablets containing the actives, into fine powder and weigh the powder. The preparer should bring to total weight with the lidocaine or lidocaine and prilocaine cream and mix well. The mixture should be milled in an ointment mill as necessary to acquire the desired smooth consistency. After which, the preparer should mix thoroughly and package appropriately.

In a further embodiment, the method may include selecting a topical base component for a transdermal cream or gel. The topical base component may include all or a portion of the local anesthetic component, such as one or more local anesthetics, e.g., lidocaine or lidocaine and prilocaine. In one example, the topical base component may include about equal amounts of lidocaine and prilocaine, such as a lidocaine 2.5% and prilocaine 2.5% cream. In another example, the topical base component may include lidocaine, such as a 5% lidocaine ointment. Other initial amounts of lidocaine and/or prilocaine may be used. The method may further include calculating an amount of actives needed and grinding up a suitable amount of the oral tablets containing the actives to obtain the calculated amount of actives for the batch. The method may further include adding the fine powder of ground oral tablets to the topical base component and milling in an ointment mill and mixing.

An example application of the above method with respect to a compounded topical composition comprising lidocaine 2.25% by weight, prilocaine 2.25% by weight, and acyclovir 8% by weight is provided. The antiviral component comprises acyclovir obtained from grinding 800 mg acyclovir oral tablets. The local anesthetic component comprises lidocaine and prilocaine obtained from a commercially manufactured/available lidocaine 2.5% and prilocaine 2.5% cream that includes the topical base component. To calculate the weight of the powders needed, each gram of compounded topical component contains 8% acyclovir (or 80 mg acyclovir) which is equivalent to 0.1005 acyclovir 800 mg oral tablets, which is equivalent to 100.5 mg total weight of acyclovir 800 mg oral tablets. Based on the determination of the amount of tablets required to obtain the desired amount of active, the number of tablets needed may be multiplied by the average weight of a tablet to obtain the weight of the tablet powder needed. The tablets are ground into a fine powder and weighed to obtain the desired weight of powder before combining. The fine powder is added to the topical base comprising lidocaine 2.5% and prilocaine 2.5% cream. To calculate the weight of the cream needed, each gram of compounded topical composition comprises 2.25% lidocaine and 2.25% prilocaine which is equivalent to 0.9 g lidocaine 2.5% and prilocaine 2.5% cream. The cream and acyclovir fine powder may be combined in an appropriate container, such as an electronic mixer jar and mixed once on normal setting. The mixture may then be milled. An Exakt 120S-450 three roll mill, front roller "1", rear roller "3" is suitable. The milled mixture may then be mixed once in the electronic mixer on normal setting. The resulting compounded topical composition may then be packaged in appropriate containers, such as tubes.

Another example application of the above method with respect to a compounded topical composition comprising lidocaine 5% by weight and acyclovir 8% by weight is provided. The antiviral component comprises acyclovir obtained from grinding 800 mg acyclovir oral tablets. The local anesthetic component comprises lidocaine obtained from a commercially manufactured/available lidocaine 5% ointment that includes the topical base component. To calculate the weight of the powders needed, each gram of compounded topical component contains 8% acyclovir (or 80 mg acyclovir) which is equivalent to 0.1005 acyclovir 800 mg oral tablets, which is equivalent to 100.5 mg total weight of acyclovir 800 mg oral tablets. Based on the determination of the amount of tablets required to obtain the desired amount of active, the number of tablets needed may be multiplied by the average weight of a tablet to obtain the weight of the tablet powder needed. The tablets are ground into a fine powder and weighed to obtain the desired weight of powder before combining. The fine powder is added to the topical base/lidocaine ointment 5%. To calculate the weight of the ointment needed, each gram of compounded topical composition comprises 4.5% lidocaine which is equivalent to 0.9 g lidocaine 5% ointment. The ointment and acyclovir fine powder may be combined in an appropriate container, such as an electronic mixer jar and mixed once on normal setting. The mixture may then be milled. An Exakt 120S-450 three roll mill, front roller "1", rear roller "3" is suitable. The milled mixture may then be mixed once in the electronic mixer on normal setting. The resulting compounded topical composition may then be packaged in appropriate containers, such as tubes.

III. Methods of Administration and Treatment

As described above, a method of treating various viral ailments related to herpes simplex and varicella zoster. Treatment may include topically administering a sufficient amount of the compounded topical composition described herein to an infected skin or mucosal area or area in which infection is sought to be prevented. The composition may be rubbed into site or may be applied using a dressing or patch. Administration at the site may be repeated twice a day, daily, for a duration of time as needed for preventative treatment or treatment of a current infection. Treatment with the compounded topical composition may reduce frequency and severity of outbreaks. Treatment with the compounded topical composition may also reduce duration of outbreaks in infected individuals. Treatment with the compounded topical composition may reduce risk of acquisition or transmission of the virus. In some embodiments, treatment with the compounded topical composition may reduce shedding.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise.

This disclosure describes various elements, features, aspects, and advantages of various embodiments, configurations, and arrangements of the compounded topical composition and methods thereof. It is to be understood that certain descriptions of the various embodiments and such configurations and arrangements thereof have been simplified to illustrate only those elements, features and aspects that are relevant to a more clear understanding of the disclosed embodiments, while eliminating, for purposes of brevity or clarity, other elements, features and aspects. Any references to "various," "certain," "some," "one," or "an" when followed by "embodiment," "configuration," or "arrangement" generally means that a particular element, feature or aspect described in the example is included in at least one embodiment. The phrases "in various," "in certain," "in some," "in one," or "in an" when followed by "embodiment", "configuration", or "arrangement" may not necessarily refer to the same embodiment. Furthermore, the phrases "in one such" or "in this" when followed by "embodiment," "configuration," or "arrangement," while generally referring to and elaborating upon a preceding embodiment, is not intended to suggest that the elements, features, and aspects of the embodiment introduced by the phrase are limited to the preceding embodiment; rather, the phrase is provided to assist the reader in understanding the various elements, features, and aspects disclosed herein and it is to be understood that those having ordinary skill in the art will recognize that such elements, features, and aspects presented in the introduced embodiment may be applied in combination with other various combinations and sub-combinations of the elements, features, and aspects presented in the disclosed embodiments. It is to be appreciated that persons having ordinary skill in the art, upon considering the descriptions herein, will recognize that various combinations or sub-combinations of the various embodiments and other elements, features, and aspects may be desirable in particular implementations or applications. However, because such other elements, features, and aspects may be readily ascertained by persons having ordinary skill in the art upon considering the description herein, and are not necessary for a complete understanding of the disclosed embodiments, a description of such elements, features, and aspects may not be provided. As such, it is to be understood that the description set forth herein is merely exemplary and illustrative of the disclosed embodiments and is not intended to limit the scope of the invention as defined solely by the claims.

What is claimed is:

1. A method of compounding a compounded topical composition, the method comprising:
   combining an antiviral component comprising one or more ground oral tablets containing an antiviral selected from acyclovir, valaciclovir, penciclovir, famciclovir, or a combination thereof and a topical local anesthetic composition containing a local anesthetic selected from lidocaine, prilocaine, or both; and
   mixing the antiviral component and the topical local anesthetic composition,
   wherein the topical local anesthetic composition comprises (a) a lidocaine 5% ointment containing the local anesthetic lidocaine in an amount 5% by weight, (b) a lidocaine 2.5% and prilocaine 2.5% cream containing the local anesthetics lidocaine and prilocaine, each in an amount 2.5% by weight, or (c) both, and
   wherein the antiviral component is combined in an amount such that the compounded topical composition comprises the antiviral in an amount between about 4% and about 12% by weight.

2. The method of claim 1, wherein the antiviral component comprises one or more ground oral acyclovir tablets containing the antiviral acyclovir, and wherein the one or more ground oral acyclovir tablets are combined in an amount such that the compounded topical composition comprises the antiviral acyclovir in an amount between about 4% and about 12% by weight.

3. The method of claim 2, wherein the one or more ground oral acyclovir tablets are combined in an amount such that the compounded topical composition comprises the antiviral acyclovir in an amount between about 6% and about 9% by weight.

4. The method of claim 2, wherein the one or more ground oral acyclovir tablets are combined in an amount such that the compounded topical composition comprises the antiviral acyclovir in an amount about 8% by weight.

5. The method of claim 3, wherein the topical local anesthetic composition comprises the lidocaine 5% ointment, and wherein the lidocaine 5% ointment is combined in an amount such that the compounded topical composition comprises the local anesthetic lidocaine in an amount greater than 4% by weight.

6. The method of claim 5, wherein the one or more ground oral acyclovir tablets are combined in an amount such that the compounded topical composition comprises the antiviral acyclovir in an amount about 8% by weight and lidocaine in an amount about 4.5% by weight.

7. The method of claim 3, wherein the topical local anesthetic composition comprises the lidocaine 2.5% and prilocaine 2.5% cream, and wherein the lidocaine 2.5% and prilocaine 2.5% cream is combined in an amount such that the compounded topical composition comprises each of the local anesthetics lidocaine and prilocaine in an amount between about 1.5% and about 2.25% by weight.

8. The method of claim 7, wherein the one or more around oral acyclovir tablets and the lidocaine 2.5% and prilocaine 2.5% cream are combined in amounts such that the compounded topical composition comprises the antiviral acyclovir in an amount about 8% by weight and each of the local anesthetics lidocaine and prilocaine in an amount about 2.25% by weight.

9. The method of claim 1, wherein the antiviral component comprises one or more ground oral acyclovir tablets containing the antiviral acyclovir and at least one of (a) one or more ground oral valaciclovir tablets containing the antiviral valaciclovir or (b) one or more ground oral famciclovir tablets containing the antiviral famciclovir.

10. The method of claim 9, wherein the topical local anesthetic composition comprises the lidocaine 5% ointment, and wherein the lidocaine 5% ointment and the one or more ground oral acyclovir tablets and the at least one of (a) the one or more ground oral valaciclovir tablets or (b) the one or more ground oral famciclovir tablets are combined in amounts such that the compounded topical composition comprises the antivirals acyclovir and the at least one of valaciclovir or famciclovir in a combined amount between about 6% and about 9% by weight and the local anesthetic lidocaine in an amount greater than 4% by weight.

11. The method of claim 10, wherein the lidocaine 5% ointment and the one or more ground oral acyclovir tablets and the at least one of (a) the one or more ground oral valaciclovir tablets or (b) the one or more ground oral famciclovir tablets are combined in amounts such that the compounded topical composition comprises the antivirals acyclovir and the at least one of valaciclovir or famciclovir in a combined amount about 8% by weight and the local anesthetic lidocaine in an amount about 4.5% by weight.

12. The method of claim 9, wherein the topical local anesthetic composition comprises the lidocaine 2.5% and lidocaine 2.5% cream, and wherein the lidocaine 2.5% and prilocaine 2.5% cream and the one or more ground oral acyclovir tablets and the at least one of (a) the one or more ground oral valaciclovir tablets or (b) the one or more ground oral famciclovir tablets are combined in amounts such that the compounded topical composition comprises the antivirals acyclovir and at least one of valaciclovir or famciclovir in a combined amount between about 6% and about 9% by weight and each of the local anesthetics lidocaine and prilocaine in an amount between about 1.5% and about 2.25% by weight.

13. The method of claim 12, wherein the lidocaine 2.5% and prilocaine 2.5% cream and the one or more ground oral acyclovir tablets and the at least one of (a) the one or more ground oral valaciclovir tablets or (b) the one or more ground oral famciclovir tablets are combined in amounts such that the compounded topical composition comprises the antivirals acyclovir and at least one of valaciclovir or famciclovir in a combined amount about 8% by weight and each of the local anesthetics lidocaine and prilocaine in an amount about 2.25% by weight.

14. The method of claim 1, wherein the antiviral component comprises at least one of (a) one or more ground oral valaciclovir tablets containing the antiviral valaciclovir or (b) one or more ground oral famciclovir tablets containing the antiviral famciclovir, and wherein the topical local anesthetic composition comprises the lidocaine 5% ointment.

15. The method of claim 14, wherein the lidocaine 5% ointment and the at least one of (a) the one ground oral valaciclovir tablets or (b) the one or more ground oral famciclovir tablets are combined in amounts such that the topical compounded composition comprises the at least one antiviral valaciclovir or famciclovir in a combined amount between about 6% and about 9% by weight and the local anesthetic lidocaine in an amount greater than 4% by weight.

16. The method of claim 15, wherein the lidocaine 5% ointment and the at least one of (a) the one ground oral valaciclovir tablets or (b) the one or more ground oral famciclovir tablets are combined in amounts such that the topical compounded composition comprises the at least one antiviral valaciclovir or famciclovir in a combined amount about 8% by weight and the local anesthetic lidocaine in an amount about 4.5% by weight.

17. The method of claim 1, wherein the antiviral component comprises at least one of (a) one or more ground oral valaciclovir tablets containing the antiviral valaciclovir or (b) one or more ground oral famciclovir tablets containing the antiviral famciclovir, and wherein the topical local anesthetic composition comprises the 2.5% and prilocaine 2.5% cream.

18. The method of claim 17, wherein the lidocaine 2.5% and prilocaine 2.5% cream and the at least one of (a) the one ground oral valaciclovir tablets or (b) the one or more ground oral famciclovir tablets are combined in amounts such that the topical compounded composition comprises the at least one antiviral valaciclovir or famciclovir in a combined amount between about 6% and about 9% by weight and each of the local anesthetics lidocaine and prilocaine in an amount between about 1.5% and about 2.25% by weight.

19. The method of claim 18, wherein the Lidocaine 2.5% and prilocaine 2.5% cream and the at least one of (a) the one ground oral valaciclovir tablets or (b) the one or more ground oral famciclovir tablets are combined in amounts such that the topical compounded composition comprises the at least one antiviral valaciclovir or famciclovir in a combined amount about 8% by weight and each of the local anesthetics lidocaine and prilocaine in an amount about 2.25% by weight.

* * * * *